Figure 1:
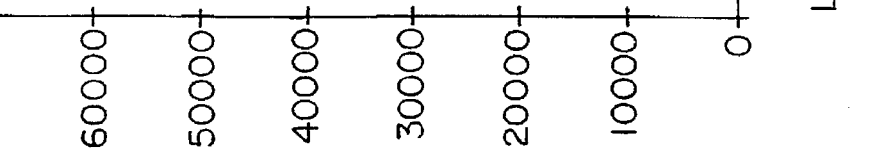

US005637300A

United States Patent [19]
Dunbar et al.

[11] Patent Number: 5,637,300
[45] Date of Patent: Jun. 10, 1997

[54] CONTRACEPTIVE VACCINE COMPRISING A GLYCOSYLATED 55 KD ZONA PELLUCIDA PROTEIN IMMUNOGEN AND METHOD OF USE OF THE SAME IN CONTRACEPTION

[76] Inventors: Bonnie S. Dunbar, 2001 Holcombe #2302, Houston, Tex. 77030; Sarvamangala V. Prasad, 5123 Jackwood, Houston, Tex. 77096

[21] Appl. No.: 285,281

[22] Filed: Aug. 3, 1994

[51] Int. Cl.$^6$ .................................................... A61K 39/00
[52] U.S. Cl. .................. 424/184.1; 424/561; 530/395; 530/388.2; 530/389.1; 514/843
[58] Field of Search ................... 514/8, 841, 843; 530/395; 424/561, 184.1

[56] References Cited

U.S. PATENT DOCUMENTS 4,996,297  2/1991  Dunbar ........................ 530/395

OTHER PUBLICATIONS

Dunbar, B.S. et al., "Identification Of An Oocyte Carbohydrate Antigen In Ovarian Carcinoma," *Molec. Biol Cell* 4:27a (1993).
Dunbar, B.S., "Morphological, Biochemical, And Immunological Characterization Of The Mammalian Zona Pellucida," In: *Mechanism and Control of Animal Fertilization* (Hartmann, J. et al., eds.) Academic Press, pp. 139–175 (1983).
Dunbar, B.S. et al., "Comparative Structure And Function Of Mammalian Zonae Pellucidae," In: *A Comparative Overview of Mammalian Fertilization* (Dunbar, B. et al., eds.) Plenum Press, pp. 97–116 (1991).
Jones, G.R. et al., "Histology Of Ovaries Of Female Rabbits Immunized With Deglycosylated Zona Pellucida Macromolecules Of Pigs," *J. Reprod. Fertil.* 95:513–525 (1992)).
Lee, V.H. et al., "Identification And Structural Characteristics Of The 75–kDa Rabbit Zona Pellucida Protein," *J. Biol. Chem.* 268:12412–12417 (1993).
Lee, V.H. et al., "Developmental Expression Of The Rabbit 55–kDa Zona Pellucida Protein And Messenger RNA in Ovarian Follicles," *Devel. Biol.* 155:371–382 (1993).
Millar, S.E. et al., "Vaccination With A Synthetic Zona Pellucida Peptide Produces Long–Term Contraception In Female Mice," *Science* 246:935–938 (1989).
Prasad, S.V. et al., "Comparison Of The Immunogenicity Of Glycosylated And Nonglycosylated Recombinant 55 Kd ZP Protein," *Biol. Reprod.* 48(suppl. 1:154 (1993)).

Rhim, S.H. et al., "Autoimmune Disease Of The Ovary Induced By A ZP3 Peptide From The Mouse Zona Pellucida," *J. Clin. Invest.* 89:28–35 (1989).
Schwoebel, E.D. et al., "Molecular Analysis Of The Antigenicity And Immunogenicity Of Recombinant Zona Pellucida Antigens In A Primate Model," *Biol. Reprod.* 47:857–865 (1992).
Schwoebel, E. et al., "Isolation And Characterization Of A Full–Length cDNA Encoding The 55–kDa Rabbit Zona Pellucida Protein," *J. Biol. Chem.* 266:7214–7219 (1991).
Skinner, S.M. et al., "The Role of Zona Pellucida Antigens In Fertility And Infertility," *Immunol., Allerg. Clin.* 10:185–197 (1990).
Timmons, T.M. et al., "Antigens Of Mammalian Zona Pellucida," In: *Perspectives in Immunoreproduction: Conception and Contraception* (Mathur, S. et al., eds.) Hemisphere Publ., pp. 242–260 (1988).
Timmons, T.M. et al., "Use Of Specific Monoclonal And Polyclonal Antibodies To Define Distinct Antigens Of The Porcine Zonae Pellucidae," *Biol. Reprod.* 36:1275–1287 (1987).
Yurewicz, E.C. et al., "Porcine Zone Pellucida ZP3α Glycoprotein Mediates Binding Of The Biotin–Labeled $M_r$ 55,000 Family (ZP3) To Boar Sperm Membrane Vesicles," *Molec. Reprod. Develop.* 36:382–389 (1993).
Yurewicz, E.C. et al., "Structural Characterization Of The $M_r$ = 55,000 Antigen (ZP3) Of Porcine Oocyte Zona Pellucida," *J. Biol. Chem.* 262:564–571 (1987).
Yurewicz, E.C. et al., "Nucleotide Sequence of cDNA Encoding ZP3α, A Sperm–Binding Glycoprotein From Zona Pellucida Of Pig Oocyte," *Biochim. Biophys. Acta* 1174:211–214 (1993).
Wassarman, P.M., "Profile Of A Mammalian Sperm Receptor," *Developmental* 108:1–17 (1990).
Wassarman, P.M. et al., "How Mouse Eggs Put On And Take Off Their Extracellular Coat," In: *Molecular Biology of Development*, Alan R. Liss, Inc. NY pp. 213–225 (1984).

*Primary Examiner*—Donald E. Adams
*Assistant Examiner*—Jacqueline G. Krikorian
*Attorney, Agent, or Firm*—Sughrue, Mion, Zinn, Macpeak & Seas

[57] ABSTRACT

Recombinant zona pellucidae proteins having altered, non-native glycosylation patterns are able to elicit the production of antibodies to matured zona pellucida proteins. Such recombinant proteins and the elicited antibodies can therefore be used in a contraceptive vaccine to prevent pregnancy in humans and animals.

2 Claims, 2 Drawing Sheets

CONTRACEPTIVE VACCINE COMPRISING A GLYCOSYLATED 55 KD ZONA PELLUCIDA PROTEIN IMMUNOGEN AND METHOD OF USE OF THE SAME IN CONTRACEPTION

CONTRACEPTIVE VACCINE

1. Field of the Invention

The present invention relates to the use of a recombinant protein as a contraceptive vaccine. More specifically, the invention relates to a recombinant zona pellucida protein that can be used to elicit antibodies that prevent sperm cells from binding to, and penetrating, the zona pellucida that surrounds egg cells. The invention is directed to the therapeutic use of such molecules, as well as to their diagnostic use. This invention was made with U.S. Government funds. The U.S. Government has certain rights in this invention.

2. Background of the Invention

The zona pellucida ("ZP") is a complex extracellular glycoprotein matrix that surrounds the mammalian oocyte (see, Wassarman, P. M., *Ann. Rev. Biochem.* 57:415–442 (1988); Dunbar, B. S. et al., In: *A Comparative Overview of Mammalian Fertilization* (Dunbar, B. et a;., eds.) Plenum Press, pp. 97–115 (1991)). The matrix is formed during the early stages of oocyte growth and follicular cell differentiation and serves to protect the oocyte and embryo until implantation in the uterine wall (Schwoebel, E. et al., *Biol. Reprod.* 47:857–865 (1992)).

In addition to protecting the oocyte, the zona pellucida plays an important role in the fertilization process (Dunbar, B. S. et al., In: *Mechanism and Control of Animal Fertilization* (Hartmann, J. et al., eds.) Academic Press, pp. 139–175 (1983)). Sperm cells are capable of binding to the zona pellucida. Fertilization occurs when a bound sperm cell penetrates the ZP. Sperm penetration of the zona pellucida is probably mediated by the limited hydrolysis of zona pellucida components by sperm enzymes such as acrosin (Dunbar, B. S. et al., *Biol. Reprod.* 32:619 (1985), and Stambaugh, Gam. Res. 1:65 (1978)). The zona pellucida remains intact after fertilization to ensure proper embryonic development and perhaps to prevent embryo fusion in the oviduct (Mintz, Science 138:594 (1962)). The zona pellucida also plays a role in preventing polyspermy (i.e., fertilization of an oocyte by multiple sperm cells). In some mammalian species, fertilization alters sperm binding to the zona pellucida, and increases its resistance to proteolytic digestion.

The zona pellucidae of different mammalian species have related structures. The zona pellucida proteins of pig and rabbit have been extensively characterized (Schwoebel, E. et al., *J. Biol. Chem.* 266:7214–7219 (1991); Lee, V. H. et al., *J. Biol. Chem.* 268:12412–12417 (1993); Lee, V. H. et al., *Devel. Biol.* 155:371–382 (1993); Dunbar, B. S., U.S. Pat. No. 4,996,297). They contain from three to five glycoproteins (Dunbar, B. S., U.S. Pat. No. 4,996,297; Schwoebel, E. et al., *Biol. Reprod.* 47:857–865 (1992); Wassarman, P. M., *Ann. Rev. Biochem.* 57:415–442 (1988); Skinner, S. M. et al., In: *Immunological Approaches to Contraception and Promotion of Fertility* (Talwar, G. P., ed.), Plenum Press, New York, pp. 251–268 (1986); Dunbar, B. S. et al., In: *A Comparative Overview of Mammalian Fertilization* (Dunbar, B. et al., eds.) Plenum Press, pp. 97–116 (1991)). These proteins vary in both size and charge.

Such studies have led to the purification of rabbit ZP proteins of approximately 50, 75 and 85 Kd apparent molecular weight, and of pig ZP proteins of approximately 35, 55 and 80 Kd. The native proteins are extensively glycosylated and appear to undergo significant post-translational modification (Dunbar, B. et al., In: *A Comparative Overview of Mammalian Fertilization* (Dunbar, B. et al., eds.) Plenum Press, pp. 97–116 (1991)).

The cDNA encoding these proteins has been cloned (Schwoebel, E. et al., *J. Biol. Chem.* 266:7214–7219 (1991); Lee, V. H. et al., *J. Biol. Chem.* 268:12412–12417 (1993); Lee, V. H. et al., Devel. Biol. 155:371–382 (1993); Dunbar, B. S., U.S. Pat. No. 4,996,297). When these cDNA molecules are expressed in a prokaryotic host (such as *E. coli*), the expression product is not glycosylated.

The nomenclature of ZP proteins is discussed in Lee, V. H. et al. (*J. Biol. Chem.* 268:12412–12417 (1993)). Natural rabbit ZP proteins are designated with an upper case "R," followed by the molecular weight of the protein, i.e., as "Rx," where "X" is the apparent molecular weight of the protein core (e.g., R55 denotes a rabbit ZP glycoprotein having a heterogeneous molecular weight of approximately 75–90 kD with a 55 kD non-glycosylated protein core). The protein core of a ZP protein is designated as "rx" (e.g., the protein core of R55 is r55). A cro-β galactosidase fusion protein of a ZP protein is designated as "recx" (e.g., the expressed fusion protein of r55 is rec55).

Despite the common morphological properties of the zona pellucidae of different mammals, the ZPs of different mammalian species have immunologically distinct regions or "epitopes" (Timmons, T. M. et al., In: *Perspectives in Immunoreproduction: Conception and Contraception* (Mathur, S. et al., eds.) Hemisphere Publ., pp. 242–260 (1988)).

Two molecules are immunologically distinct when an antibody that is capable of binding to one molecule is incapable of binding to the other. Humans and other animals have the ability to discriminate between their own ("native") molecules and "foreign" molecules (such as the proteins present on the surface of pathogenic bacteria or viruses). A molecule that is recognized as "foreign" provokes the immune system to produce antibodies that are capable of binding to the foreign molecule. Foreign molecules fall into two classes: "immunogens" and "haptens." An immunogen is a molecule whose presence in an animal is capable of inducing the animal's immune system to produce antibodies. In contrast, a hapten is capable of being bound by an antibody, but is not capable of eliciting high titer antibody formation. The immunogenicity of a hapten (i.e., the capacity of the molecule to induce antibody production) can be enhanced by conjugating it to a larger molecule. The nature and structure of antibodies, and the tenets of immunology are disclosed by Davis, B. D. et al. (In: *Microbiology*, 2d Ed., Harper & Row, New York (1973)). Antibodies play a central role in the humoral response to infection (Takatsu, K., *Microbial Rev* 35:593–606 (1991)).

Exposure of an animal to a preparation containing its own ZP protein (i.e., "alloimmunized") will not elicit the production of anti-ZP protein antibodies (Skinner, S. M. et al., *J. Reprod. immunol.* 12:81–92 (1987)). In contrast, if a mammal is exposed to a ZP protein of a different species (i.e. "heteroimmunized"), it will respond by producing antibodies against the foreign ZP protein.

Some of the antibodies elicited through such heteroimmunization are capable of reducing fertility (Porter, C. W. *Inti. J. Fertil.* 10:257–260 (1965); Porter, C. W. et al., *Inti. J. Fertil.* 15:171–176 (1970); Shivers, C. A. et al., *Science* 178:1211–1213 (1972); Skinner, S. M. et al., *immunol.*,

*Allerg. Clin.* 10:185–197 (1990); Dunbar, B. S. et al., In: *Mechanism and Control of Animal Fertilization* (Hartmann, J. et al., eds.) Academic Press, pp. 139–175 (1983)). The immunization can, however, also elicit the production of antibodies that interrupt and impair follicular growth at the time the ZP matrix is formed (Schwoebel, E. et al., *Biol. Reprod.* 47:857–865 (1992); Skinner, S. M. et al., *Endocrinol.* 115:2418–2432 (1984); Rhim, S. H. et al., *J. Clin. Invest.* 89:28–35 (1992)).

The observation that some of the antibodies elicited through ZP heteroimmunization were capable of reducing fertility suggested that ZP proteins could be used as a contraceptive vaccine (Shivers, C. A., In: *Immunoiogical Influence on Human Fertility*, (Boeticher, B., ed.), Academic Press, New York, pp. 13–24 (1977); Dunbar, B. S. et al., In: *Mechanism and Control of Animal Fertilization* (Hartmann, J. et al., eds.) Academic Press, pp. 139–175 (1983); Dunbar, B. S., U.S. Pat. No. 4,996,297).

"Immunocontraception" involves the use of immunological methods of intervention to cause contraception or sterilization. Early attempts to develop immunocontraceptive methods were not been very successful. Those attempts included the use of antibodies against naturally occurring circulating peptide hormones such as human chorionic gonadotrophin (hCG) and follicle stimulating hormone (see, *Immunological Approaches to Contraception and Promotion of Fertility*, (Talwan, G. P., ed.) Plenum Press, New York (1986)). Immunocontraception utilizing antibodies against normally "circulating" hormones poses the problem that immune complexes might form which would bring about undesirable tissue damage. Furthermore, immunization with "circulating" hormones has not proven to be sufficiently effective in inhibiting fertility.

The development of an effective and economical ZP-based vaccine has been complicated by several factors. Efforts have been hindered by the difficulty of obtaining sufficient material to produce the quantities of antigen or antibodies that would be needed in order to produce a suitable vaccine.

In order to determine whether recombinant ZP proteins could be employed as immunogens, Schwoebel, E. et al. constructed a gene fusion that expressed a (cro-β-galactosidase-r55) rec55 fusion protein and evaluated its immunogenicity. The non-glycosylated recombinant proteins produced in bacteria did not elicit antibodies when provided to recipient female cynomolgus monkeys (Schwoebel, E. et al., *Biol. Reprod.* 47:857–865 (1992)). Although such antibodies could be elicited by conjugating the recombinant molecules to an immunogenic protein (such as protein A or keyhole limpet hemocyanin) the titers of the antibodies were unstable, and required regular boosting in order to be maintained (Schwoebel, E. et al., *Biol. Reprod.* 47:857–865 (1992)).

Moreover, as indicated above, heteroimmunizations of ZP proteins elicit antibodies that undesirably impair follicle development. Researchers have attempted to identify and segregate those immunological domains of the ZP proteins that are involved in sperm binding from those that impair follicle cell development, however such efforts have not yet led to the identification of the relevant domains (Schwoebel, E. et al., *Biol. Reprod.* 47:857–865 (1992)). Indeed, the domain(s) involved in sperm binding may be identical or overlap with those that impair follicle cell development, and thus may not be separable at all.

As indicated above, the zona pellucida (ZP) is a unique extracellular glycoprotein matrix that surrounds the oocyte of all mammalian species and is composed of three major glycoproteins in most species. These glycoproteins exhibit species variation in their Immunochemical, biochemical and biological properties (Timmons, T. M. et al., In: *Gamete Interaction: Prospects for Immunocontraception* (Alexander N. et al., eds) John Wiley & Son, New York; pp. 277–292 (1990); Dunbar B. S. et al., In: *A Comparative Overview of Mammalian Fertilization* (Dunbar, B. S. et al., eds) Plenum Press, New York pp. 97–116 (1991)). The different ZP glycoproteins are expressed in a specific pattern during oogenesis and follicular development and mediate critical events during fertilization (Wolgemuth, D. J. et al., *Dev. Biol.* 106:1–14 (1984); Lee, V. H. et al., *Dev. Biol.* 155:371–382 (1993); Dean, J., *J. Clin. Invest.* 89:1055–1059 (1992); Wassarman, P. M., *Biol. Reprod.* 46:186–191 (1992) ). Following ovulation of the mature egg, the ZP proteins play important roles throughout the different stages of the fertilization processes and early embryonic development (Wasserman, P. M., *Biol. Reprod.* 46:186–191 (1992);. Yanagimachi, R., In: The Physiology of Reproduction, Vol. 1 (Knobil E., et al., eds), Raven Press, New York, pp. 135–185 (1988)).

Complex carbohydrates of the ZP glycoconjugates have been implicated in species-specific sperm-egg interaction (Florman, H. M. et al., *Cell* 41:313–324 (1985); Bleil, J. D. et al., *Proc. Natl. Acad. Sci* (U.S.A.) 86:6778–6782 (1988); Miller, D. J. et al., *Molec. Reprod. Dev.* 33:182–188 (1990); Yurewicz, E. C. et al., *Molec. Reprod. Dev.* 33:182–188 (1991)). Because immunizations with specific ZP proteins have been shown to be able to elicit antibodies that can inhibit sperm binding and subsequent fertilization, ZP proteins have been considered as a target for immunocontraception (Skinner, S. M. et al., In: *Fertility and Infertility. Immunology and Allergy Clinics of North America* 10:185–197 (1989);. Millar, S. E. et al., *Science* 246:935–938 (1989); Sacco, A. G. et al., *Amer. J. Primatol.* 24:15–28 (1991)).

Many studies have demonstrated that the immunogenicity and antigenicity of ZP glycoproteins is extremely complex and the immune response depends on the species from which the immunogen is derived as well as on the target animal being immunized. Heteroimmunization of rabbits or other species with total pig ZP proteins or with purified ZP3 (a 55 kD family of porcine ZP proteins) has been shown to result in the elicitation of antibodies to "self" ZP antigens that can interfere with follicular development as well as fertility (Sacco, A. G. et al., *Amer. J. Primatol.* 24:15–28 (1991); Gulyas, B. J. et al. *Gamete Res.* 4:299–307 (1983); Skinner, S. M. et al., *Endocrinol.* 115:2418–2432 (1984); Sehgal, S. et al., *Pathol.* 21:105–110 (1989): Dunbar, B. S. et al., *Fertil. Steril.* 52:311–318 (1989); Upadhyay, S. N. et al. *Biol. Reprod.* 41:665–673 (1989); Mahi-Brown, C. A. et al., *Amer. J. Reprod. Immunol. Microbiol.* 18:94–103 (1988); Jones, G. R. et al., *J. Reprod. Fertil.* 95:513–525 (1992)).

In addition, studies using purified native (Jones, G. R. et al., *J. Reprod. Fertil.* 95:513–525 (1992)) or synthetic ZP peptides (Rhim, S. H. et al., *J. Clin. Invest.* 89:28–35 (1989) have identified specific ZP proteins or peptides that elicit antibodies which alter ovarian follicular development or cause autoimmune cophoritis (Jones, G. R. et al., *J. Reprod. Fertil.* 95:513–525 (1992)).

Although studies using purified native procine ZP protein (Jones, G. R. et al., *J. Reprod. Fertil.* 95:513–525 (1992)) or synthetic mouse ZP peptides (Millar, S. E. et al., *Science* 246:935–938 (1989) have identified specific ZP proteins or peptides which elicit antibodies that inhibit sperm binding to ZP without altering ovarian follicular development, such efforts have failed to identify a suitable contraceptive vaccine. Millar, S. E. et al. (*Science* 246:935–938 (1989)) evaluated the contraceptive effect imparted by administering a KLH conjugate of a mouse ZP protein heptapeptide. A long-term contraceptive effect was observed in only 50% of immunized animals. More significantly, Millar, S. E. et al. determined that this immunogen was not recognized in other species, and hence would not be expected to act as a contraceptive in species other than rodents (Millar, S. E. et al., *Science* 246:935–938 (1989). Jones, G. R. et al. (*J. Reprod. Fertil.* 95:513–525 (1992)) compared glycosylated, partially deglycosylated and fully deglycosylated procine ZP proteins as contraceptive immunogens. Gylcosylated immunogens were found to cause undesired impairment of follicular development (Jones, G. R. et al., *J. Reprod. Fertil.* 95:513–525 (1992)). The partially deglycoslylated immunogens employed by Jones, G. R. et al. (*J. Reprod. Fertil.* 95:513–525 (1992)) were found to cause a decrease in follicle number, although they did not appear impair follicular development (Jones, G. R. et al., *J. Reprod. Fertil.* 95:513–525 (1992)). In contrast, fully degycosylated proteins did not exhibit such adverse reactions (Jones, G. R. et al., *J. Reprod. Fertil.* 95:513–525 (1992)).

Although the above-described studies have shown that heteroimmunization is extremely effective in generating antibodies, alloimmunization of female rabbits with rabbit ZP proteins does not elicit a significant immune response as evaluated by detection of such circulating antibodies (Skinner, S. M. et al., *J. Reprod. Immunol.* 12:81–92 (1987); Sacco, A. G. et al., J. Reprod. Fertil. 76:575–586 (1986)). In addition, it has been shown that deglycosylated ZP proteins are not as immunogenic as the native ZP proteins (Dunbar, B. S. et al., *Fertil. Steril.* 52:311–318 (1989); Sacco, A. G. et al., J. Reprod. Fertil. 76:575–586 (1986)). It has also been shown that immunization of cynomolgus monkeys with bacterially expressed, recombinant rabbit ZP proteins which are not glycosylated, does not elicit significant antibody titers unless these proteins are conjugated to an immunogenic protein (Schwoebel, E. D. et al., *Biol. Reprod.* 47:857–865 (1992)). Thus, the studies indicate that native glycosylated ZP proteins are more immunogenic then deglycosylated ZP proteins.

Prasad, S. V. et al. (Prasad, S. V. et al., *Biol. Reprod.* 48(suppl. 1:154 (1993)) reported that the low immunogenicity of the rec55 fusion protein could be overcome by expressing the protein as a glycoprotein using a baculovirus—Sf9 insect cell expression system. The expressed protein (termed "BV-55") was found to exhibit abnormal glycosylation, and to be immunogenic in rabbits (Prasad, S. V. et al., *Biol. Reprod.* 48(suppl. 1:54 (1993)).

Despite the above-described practical impediments, immunologically based methods of contraception are preferable to other commercially available methods such as surgical sterilization or birth control pills (for humans and pets) in which there is a continuous expense for medication which must be used and purchased on a regular basis and are only indicated for use on a temporary basis. Thus, a considerable need exists for preparations that can induce a transient or permanent contraceptive state in an individual and which can be provided in a safe, reliable and cost effective manner.

It would thus be disirable to have a contraceptive agent that could impart long term infertility in recipients. It would further be desirable for such an agent to be substantially free of adverse side effects, and, in particular, to mediate infertility without disrupting the normal hormonal regulation.

The present invention provides such a contraceptive agent, as well as methods for its use.

SUMMARY OF THE INVENTION

The present invention concerns the use of a recombinant 55 kD rabbit ZP protein (BV-55) as a contraceptive agent to prevent pregnancy. The contraceptive agent may be used to confer either passive or active immunity to ZP proteins, and thus may be used to provide either short term or long term contraception. The invention also concerns the antibodies that bind to the BV-55 protein, and to immunoassay methods for their detection and quantification.

In detail, the invention provides a contraceptive vaccine comprising an immunogenically effective amount of an antibody elicited in response to the administration of a glycosylated 55 kD rabbit zona pellucida protein immunogen, wherein the immunogen lacks a lactosaminoglycan type structure, and wherein the immunogen elicits a female recipient to produce antibodies that inhibit the binding of sperm to egg cells by binding to the zona pellucida of the female's oocytes, but does not elicit antibodies that interfere with the development of the female's follicular cells, or the number of such cells produced.

The invention further provides a method of contraception which comprises administering to a female an immunogenically effective amount of an agent selected from the group consisting of:

(A) a glycosylated 55 kD rabbit zona pellucida protein immunogen, wherein the immunogen lacks Lactosaminoglycan type structures, and wherein the immunogen elicits a female recipient to produce antibodies that inhibit the binding of sperm to egg cells by binding to the zona pellucida of the female's oocytes, but does not elicit antibodies that interfere with development of the female's follicular cells; and (B) an antibody elicited by the immunogen (A), wherein the antibody inhibits the binding of sperm to egg cells by binding to the zona pellucida of the female's oocytes, but does not interfere with development of the female's follicular cells.

The invention particularly concerns such vaccines and methods that exploit a rabbit 55 kD zona pellucida protein as immunogen, especially when such a protein is expressed in insect cells. The invention is particularly drawn to the use of BV-55 as an immunogen for such vaccines and methods.

BRIEF DESCRIPTION OF THE FIGURES

FIG. 1 shows the antibody liters (presented as maximum serum dilutions giving a positive reading over control) elicited in cynomolgus monkeys that had been immuinized with either BV-55, a non-glycosylated pEX expressed recombinant 55 kD protein ("rec55-pEX"), or adjuvant alone.

FIG. 2 shows the ability of anti-BV-55 antibodies to inhibit the binding of rabbit sperm to rabbit egg. Data are mean percent bound relative to controls. Error bars are±Standard Error of the Mean. Asterisks indicate that the data is significantly different from the controls at $p<0.0005$ (paired Students t Test). "GP-α-BV-55" denotes gulnea pig antisera generated against BV-55; "GP-α-BV-55 Fab" denotes Fab fragments from GP-α-BV-55; "GP-α-Sf9" denotes a control guinea pig antisera generated against Sf9 insect cells; "S-α-hsRZ" denotes a control antisera from sheep immunized with heat solubilied rabbit ZP.

DETAILED DESCRIPTION OF THE INVENTION

I. The BV-55 Immunogen and Its Equivalents

The present invention relates to a contraceptive agent for decreasing or eliminating the possibility of pregnancy in humans, and other mammals (particularly, cattle, rabbits pigs, dogs, cats, rodents, and non-human primates). As used herein, a "contraceptive agent" is an agent which decreases or eliminates the possibility of pregnancy. An agent decreases the possibility of pregnancy if its administration to a recipient female lessens the frequency or probability of sperm-egg binding by at least 50%, and more preferably by at least 90%. The contraceptive agents of the present invention comprise ZP proteins that are produced in a non-natural (i.e. "heterologous") cell.

When produced in a heterologous source, a protein may exhibit either a "native glycosylation pattern," or a "non-native glycosylation pattern." As used herein, an Immunogen is said to exhibit a "native glycosylation pattern" if the glycosylation pattern of the protein is not detectably different from the glycosylation pattern exhibited by the same protein when that protein is produced in its natural host. In contrast, an immunogen is said to exhibit a "non-native glycosylation pattern" if the glycosylation pattern of the protein is detectably different from that exhibited by the naturally occurring protein.

Insert cells and mammalian cells have been believed to have similar capacities to glycosylate proteins, and to produce proteins having substantially the same patterns and extent of glycosylation (Summers, M. D., U.S. Pat. No. 5,278,050); Summers, M. D. et al., In: *A Manual of Methods for Baculovirus Vectors and Insect Cell Culture Procedures*; Texas Agricultural Experiment Station Bulletin No. 1555 (1987); Cook, N. J. et al., PCT Patent Appln. WO94/10297; Iatrou, K., PCT Patent Appln. WO94/00585; Baecker, P. A. et al., U.S. Pat. No. 5,272,063; Ghiasi, H. et al., European Patent Publication No: 568,178).

The invention derives, in part, from the recognition that mammalian ZP proteins expressed via recombinant means in insect cells exhibit an altered pattern of glycosylation (relative to the pattern exhibited by the ZP proteins when produced in their natural hosts). Moreover, the difference in glycosylation is sufficient to cause the ZP proteins to be Immunogenic when injected into mammals. Such proteins thus act as immunogens to induce the production of antibodies that are capable of binding to the zona pellucida, and preventing thereby penetration of sperm.

Thus, in one embodiment, the invention is directed to the production of ZP immunogens by producing ZP proteins having non-native patterns of glycosylation.

"BV-55" is the preferred ZP protein immunogen of the present invention. The protein is formed from the expression, in insect cells, of cDNA that encodes the 55 kD rabbit ZP protein (see Prasad, S. V. et al., *Biol. Reprod.* 48(suppl. 1:154 (1993)).

The sequence of cDNA encoding the 55 kD rabbit ZP protein is disclosed in U.S. Pat. No. 4,996,297 (with reference to a protein of approximately 50 kD), and in Schwobel, E. et al. (*J. Biol. Chem.* 266:7214–7219 (1991)). The sequence of the 55 kD protein is disclosed in Schwobel, E. et al. (*J. Biol. Chem.* 266:7214–7219 (1991)).

A bacteriophage lambda vector (λgt11-P3) that contains such cDNA in a 1.7 kb Eco RI insert was deposited on Oct. 8, 1987 with the American Type Culture Collection 12301, Parklawn Drive, Rockville, Md. 20852, U.S. The deposited vector has been designated as accession number ATCC 40378. In addition, a recombinant baculovirus (designated "BV-55") which expresses the BV-55 immunogen was deposited under the terms of the budapest with the American Type Culture Collection on Aug. 2, 1994, as Deposit Accession No. VR2467.

Although BV-55 has the same amino acid sequence as the 55 kD rabbit ZP protein of U.S. Pat. No. 4,996,297 and of Schwobel, E. et al. (*J. Biol. Chem.* 266:7214–7219 (1991)), the glycosylation pattern of BV-55 differs from that which the rabbit protein exhibits when isolated from the zona pellucidae of rabbits. "BV-55" thus illustrates an Immunogen that has a "non-native glycosylation pattern."

Indeed, the pattern of glycosylation of BV-55 is sufficiently distinct from that of R55 (i.e. the natural pattern) that the expressed BV-55 rabbit ZP protein is able to elicit an autoimmune response in female rabbits, whereas R55 does not.

Although BV-55 is the preferred immunogen of the present invention, proteins other than the 55 kD rabbit protein may be employed as immunogens. In particular, ZP proteins having homology to the rabbit 55 kD protein including human, cat, dog, monkey and pig ZP proteins are sufficiently homologous to the rabbit protein that they will function as equivalent immunogens for the purposes of the present invention. A protein is the equivalent of BV-55 if it exhibits the above-described attributes of BV-55. ZP proteins of other mammals that can function as immunogens when expressed in insect cells may be employed as equivalents of BV-55.

In addition to cDNA that encode such equivalents of the BV-55 immunogen, cDNA molecules that encode "analogs" or other equlvalents of this protein may alternatively be employed. The term "analog" is intended to include proteins or polypeptides which differ from a zona pellucida protein by addition, deletion or substitution of one or more amino acids but which substantially retain the antigenic and biologic activity of the zona pellucida protein. These analogs include selected determinant sites of the zona pellucida protein. These antigenic preparations can be used to immunize an animal such that antibodies are produced thereto. Equivalent proteins may be used in lieu of, or in concert with, BV-55. Examples of analogs of BV-55 include fragments of the BV-55 immunogen; fragments of rec55 produced in insect cells; rec55 protein produced in insect cells, fragments of other ZP proteins when expressed in insect cells, etc., which exhibit the above-described attributes.

Such equivalent proteins and BV-55 analogs may be readily identified by their capacity to bind to anti-BV-55 antibodies. Additionally, other equivalents of BV-55 may be identified by selecting other ZP proteins, and expressing such proteins (or fragments thereof) in insect cells.

Preferably, the expression of such ZP-encoding cDNA or equivalent is accomplished by incorporating the cDNA into a commerically available baculovirus vector, such as PVL1393 (Invitrogen, San Diego, Calif., US), and transfecting the resultant vector into Sf9 insect cells, or their equivalents (e.g., SF21 cells, High Five™ Cells (Trichoplusiani), MG1 cells, etc.). Methods for accomplishing such transfection, and for culturing the insect cells are described by Summers, M. D. (U.S. Pat. No. 5,278,050), herein incorporated by reference. Additional references relating to baculovirus-insect cell expression systems include Summers, M. D. et al. (In: *A Manual of Methods for Baculovirus Vectors and Insect Cell Culture Procedures*; Texas Agricultural Experiment Station Bulletin No. 1555 (1987)), Cook, N. J. et al. (PCT Patent Appln. WO94/10297), Iatrou, K. (PCT Patent Appln. WO94/00585); Baecker, P. A. et al. (U.S. Pat. No. 5,272,063) and Ghiasi, H. et al., (European Patent Publication No: 568,178), all of which references are herein Incorporated by reference. The Sf9 insect cell line is a preferred host for expressing and obtaining such Immunogens. The Sf9 insect cell line can be obtained from the American Type Culture Collection, Rockville, Md., US, as deposit accession number ATCC CRL 1711. Other cells, such as plant cells may also be employed in order to produce immunogens having non-native glycosylation patterns.

When used as an immunogen, it is desirable to employ a "substantially pure" molecule. The term "substantially pure" when applied to the zona pellucida protein of the present invention means that the protein is essentially free of other ovarian proteins normally associated with the zona pellucida protein in its natural state and exhibiting constant and reproducible electrophoretic or chromatographic response, elution profiles, and antigen activity. The term "substantially pure" is not meant to exclude artificial or synthetic mixtures of the zona pellucida protein with other compounds.

As indicated, the 55 kD rabbit ZP protein is a preferred immunogen, especially when expressed in insect cells. Recombinantly produced 55 kD rabbit ZP protein (r55 or rec55) has several attributes which render it a potential immunogen of a contraceptive vaccine;

(1) Antisera from monkeys immunized with rec55 rabbit ZP protein are found to inhibit monkey sperm from binding to monkey eggs. Thus, the protein component of BV-55 is not only immunogenic in primates, but is capable of eliciting the production of antibodies that can inhibit fertilization.

(2) rec55 does not elicit the production of antibodies that interfere with normal follicular development or hormonal function of the ovary. This attribute is significant for contraceptive methods that are desired to be reversible, since, as discussed above, other ZP immunogens have been found to elicit the production of antibodies that undesirably interfere with normal follicular development or hormonal function.

(3) The amino acid sequence of the rabbit 55 kD ZP protein is similar to the pig ZP3α sperm receptor protein (Sacco, A. G. et al., *Biol Reprod* 41:523–532 (1989); Schwoebel, E. et al., *J. Biol. Chem.* 266:7214–7219 (1991), all herein incorporated by reference).

(4) Antibodies to native rabbit R55 protein elicits the production of antibodies that cross-react with native human ZP proteins. The ability of the rabbit protein to elicit cross-reacting molecules permits its use as a human contraceptive agent.

One aspect of the present invention concerns the recognition that BV-55 possesses the above-described attributes of r55 or rec 55 but in addition is capable of eliciting high titers of antibodies without being conjugated to a foreign carrier. Moreover, such elicited antibodies do not elicit antibodies that interfere with the development of the female's follicular cells, or the number of such cells produced. It thus comprises a preferred immunogen for a contraceptive vaccine. The invention shall therefore be described with reference to this preferred immunogen.

II. The Uses of the Molecules of the Present Invention

A distinct advantage of zona pellucida protein immunocontraception is the fact that low titers of zona pellucida antibodies will block fertilization. This is due to the localized and specific nature of the site of action of the immunocontraceptive antibody and the limited occurrence of naturally occurring zona pellucida protein in the individual in which fertilization is to be blocked. The zona antigens studied to date are tissue specific and are fixed in the ovary so they do not circulate. In contrast, the hormone proteins circulate throughout the individual, occur at much higher levels, and the levels of circulating antigen vary greatly depending upon the physiological state of the individual. In addition, the levels of sperm antigens which must be blocked for sperm antigen immunocontraception to be efficient is variable, being dependent upon the amount of sperm in the vaginal canal and uterine cavity.

In one embodiment of the present invention, contraception is achieved by administering an agent of the present invention (e.g., BV-55), alone, or as a component of a phamaceutical composition, to a recipient female. Such administration may be accomplished by injection, by long release implants, by rapid infusion, intravenously, by nasopharyngeal absorption, by dermal absorption, or orally. Preparations for parenteral administration include sterile or aqueous or non-aqueous solutions, suspensions, and emulsions. Examples of non-aqueous solvents include propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable liquid dosage forms include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

Such administration is termed "active immunization," since the administration of the agent provokes the recipient's immune system into producing anti-ZP antibodies. Active immunization promotes long term contraceptive activity. Permanent contraception can be accomplished by supplementing an initial administration with one, two or more subsequent "booster" administrations of the immunogen. Many different techniques exist for the timing of the immunizations when a multiple immunization regimen is utilized. It is possible to use the antigenic preparation of the invention more than once to increase the levels and diversity of expression of the immunoglobulin repertoire expressed by the immunized animal. Typically, if multiple immunizations are given, they will be spaced 1 month to 6 months apart.

In one embodiment, the immunogenic preparations will include an adjuvant. Adjuvants are substances that can be used to non-specifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete Adjuvants), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (e.g., wax D from Mycobacterium tuberculosis, as well as substances found in Corynebacterium parvum, Bordetella pertussis, and members of the genus Brucella).

When a homogeneous antibody (e.g., a monoclonal antibody (MAb)) is used as an immunogen, portions of the molecule may be recognized as antigenic determinants by the responding immunized host. The unique combination sites of the homogeneous antibody which would recognize its antigenic determinants is termed the "idiotype." Antibodies produced against these sites of the antibody are therefore termed "anti-idiotype." These antibodies may have "internal images" and therefore can have activities which mimic the original immunogen (Sege, K. et al., *Proc. Soc. Natl. Acad. Sci. (USA)* 75:2443 (1978); Schreiber et al., *Proc. Soc. Natl. Acad. Sci. (USA)* 77:7385 (1980); Erlanger et al., *Immunol. Rev.* 94: 25 (1986)). Thus, in yet another embodiment of the present invention, the anti-BV-55 monoclonal antibodies may be used as immunogens, and thus enable the isolation of anti-idiotypic antibodies whose domains mimic those of BV-55. Such antibodies may be used in the same manner as BV-55 to confer active immunity to a recipient.

When an individual is immunized with ZP antigens or anti-idiotypic antibodies prior to the maturation of the ovaries, ovarian development is severely hindered and permanent irreversible sterilization may occur. This is a particularly desirable method of causing immunocontraception in animals, particularly pets such as cats and dogs, when reproduction is undesirable. The use of ZP immunocontraception in such cases obviates the need for costly and potentially dangerous surgical contraception.

In an alternative embodiment, contraception can be accomplished via "passive immunization." The term "passive immunization" denotes that the immunization is accomplished via the administration of anti-ZP antibodies (as opposed to the ZP immunogen used in active immunization protocols). Passive immunization is desirable for establishing short term contraception (e.g., six months or less). Passive immunization is also desirable in circumstances in which immediate contraceptive effect is required, such as after sexual intercourse or rape. Passive immunization is also desirable when the recipient is immune-compromised (such as an individual recovering from transplant therapy, chemotherapy, or an individual suffering from AIDS, etc.).

In one embodiment, such antibodies may be polyclonal antibodies raised against the BV-55 immunogen. The host species for such antibodies may be any mammal. Suitable polyclonal antibodies may be prepared, for example, by immunizing female rabbits or castrated male sheep with 50 to 500 μg of BV-55 protein. The immunogen is preferably suspended in water and emulsified with Freund's Complete Adjuvant prior to injection. Animals may be injected in multiple intradermal sites (preferably subcapsularly) and are preferably boosted after 4 weeks with BV-55 protein (in Freund's Incomplete Adjuvant) at one half the amount of protein used for the initial immunization. If desired, additional boosts at monthly intervals using Freund's Complete Adjuvant may be given to obtain even higher antibody titers.

In lieu of polyclonal antibodies, the BV-55 immunogen may be used to elicit monoclonal antibodies (Koprowski, H. et al., U.S. Pat. Nos. 4,172,124 and 4,196,265). Murine monoclonal antibodies are particularly preferred. BALB/c mice are preferred for this purpose, however, equivalent strains may also be used. The animals are preferably immunized with approximately 25 μg of affinity purified BV-55 protein (or an equivalent thereof) that has been emulsified a suitable adjuvant (such as TiterMax adjuvant (Vaxcel, Norcross, Georgia)). Immunization is preferably conducted at two intramuscular sites, one intraperitoneal site, and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-BV-55 antibodies. Preferably, a direct binding ELISA is employed for this purpose.

Most preferably, the mouse having the highest antibody titer is given a third i.v. injection of approximately 25 μg of BV-55 protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting hybridoma clones may then be screened for their capacity to produce monoclonal antibodies ("mAbs) to SDI protein, preferably by direct ELISA.

Thus, in another embodiment, this invention contemplates a novel continuous hybridoma cell line which expresses monoclonal anti-BV-55 antibody, as well as the use of such cell line to produce such antibody. The present invention also contemplates a novel continuous hybridoma cell line which expresses anti-ZP antibody obtained by immunizing an animal with BV-55 protein. Antibody may be obtained through the in vitro culturing of the cells, or by injecting the cells into a histocompatable animal where they can proliferate and produce high levels of anti-ZP antibody. Such antibody can be recovered from the animal's ascites fluid, lymph, blood, etc.

The antibodies administered in a passive immunization procedure are themselves "foreign" molecules. Thus, they will eventually be eliminated from the recipient's circulation.

Thus, by way of illustration using a human recipient, the administration of murine anti-BV-55 antibodies will ultimately elicit the production of anti-mouse antibodies by the recipient's immune system. Such antibodies will eliminate the contraceptive effect imparted by the murine anti-BV-55 antibodies. Thus, the state of infertility caused by passive immunizations is reversible, and such immunization is preferred when a permanent contraceptive state is not desired.

The rate at which the anti-BV-55 antibodies will be removed from the circulation can be controlled by altering the extent to which the antibodies differ from those native to the recipient. Thus, the antibodies may be "humanized" in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., PCT Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985); Shaw et al., *J. Natl. Cancer Inst.* 80:1553–1559 (1988); all of which references are incorporated herein by reference). General reviews of "humanized" chimeric antibodies are provided by Morrison, S. L. (*Science*, 229:1202–1207 (1985)) and by Oi, V. T. et al., *BioTechniques* 4:214 (1986); which references are incorporated herein by reference). Alternatively, recently disclosed methods for producing human monoclonal antibodies may be employed in order to attenuate or prevent the elimination of the anti-BV-55 antibodies from the recipient's circulation.

Suitable "humanized" antibodies can alternatively be produced by substitution of an antibody's complementarity determining regions (Jones, P. T. et al., *Nature* 321:552–525 (1986); Verhoeyan et al., *Science* 239:1534 (1988); Beidler, C. B. et al., *J. Immunol.* 141:4053–4060 (1988); all of which references are incorporated herein by reference).

The above-described antibody molecules are divalent (i.e. possess the capacity to bind two ZP molecules). The invention also includes derivatives and modified immunoglobulins. Thus, in one embodiment, such molecules will comprise fragments (such as (F(ab'), F(ab')$_2$) that are produced, for example, by the proteolytic cleavage of the antibodies. The anti-zona pellucida monoclonal antibody binding determinant genes may be cloned and modified by recombinant DNA technology to produce "single chain antibodies" directed against ZP antigenic determinants (Cabilly et al., Proc. Acad. Sci. USA 81:3273 (1984); Boss et al., Nucleic Acids Research 12: 3791 (1984)). Such molecules may be used in passive immunization protocols to achieve contraception.

Any of the above-described active or passive immunization protocols may be combined in order to provide both active and passive immunizations.

Generally, the dosage of ZP recombinant protein administered to an animal will vary depending on such factors as age, condition, and whether temporary contraception or permanent ovarian castration is the object of the immunization, and other variables which can be readily ascertained and adjusted by one of ordinary skill in the art. The dosages of the antigenic preparations of the invention can vary from 0.01–5 g ZP antigen per dose, although greater or lesser doses may be employed if desired. The dose will be an "immunogenically effective amount." As used herein, an "immunogenically effective amount" is meant to denote that amount of immunogen which is necessary to induce the production in an animal of antibodies which will bind to zona pellucida epitopes. Fully conventional methods for stimulating the production of antibodies may be used to elicit antibodies to the immunogens of the present invention. Examples of such methods can be found in Dean (PCT Patent Application Publication No. WO90/15624), and in Harris, J. D. et al. (PCT Patent Application Publication No. WO94/11019) both of which references are herein incorporated by reference.

One way of determining whether an animal has been immunized is by determining the animal's immune status with respect to zona pellucida antigens. This evaluation can be done by assaying the titer of ZP-binding antibodies in a sample of, for example, blood, serum, urine, saliva, teardrop, etc. Most preferably, an enzyme-linked immunosorbent assay ("ELISA") that is capable of detecting antibodies to the BV-55 immunogen or its equivalent will be used for this purpose (Drell, et al., *Biol. Reprod.* 30:445 (1984); *ELISA and Other Solid Phase Immunoassays* (Kemeny, D. M. et al., Eds.), John Wiley & Sons, N.Y. (1988), Incorporated by reference herein). Such an assay can determine when the individual's antibody titer to BV-55 is sufficiently high to ensure immunization and protect against pregnancy.

As will be understood from the well-known principles of immunoassays, alternative formats, such as immunometric assays (also known as a "two-site" or "sandwich" assays), including both "forward," "simultaneous" and "reverse" assays may be employed (Fackrell, *J. Clin. Immunoassay* 8:213–219 (1985); Yolken, R. H., *Rev. Infect. Dis.* 4:35 (1982); Collins, W. P., In: *Alternative Immunoassays*. John Wiley & Sons, N.Y. (1985); Ngo, T. T. et al., In: *Enzyme Mediated Immunoassay*, Plenum Press, N.Y. (1985)).

For example, in a "forward" assay, BV-55 would be bound to a solid support (such as a microtiter plate, test tube, dipstick, etc.), and then first contacted with the sample being evaluated for the presence of anti-BV-55 antibody under conditions that permit the formation of a binary solid phase BV-55-antibody complex. After incubation and washing, the support would be placed in contact with a quantity of labeled BV-55 (which functions as a "reporter molecule"). After a second incubation period to permit the labeled BV-55 to complex with the immobilized BV-55 through the unlabeled antibody, the solid support would be washed a second time to remove the unreacted labeled BV-55. This type of forward sandwich assay may be a simple "yes/no" assay to determine whether anti-BV-55 antibodies are present or may be made quantitative by comparing the amount of retained labeled BV-55 with that obtained for a standard containing known quantities of anti-BV-55 antibody. "Two-site" or "sandwich" assays are described by Wide, In: *Radioimmune Assay Method*, (Kirkham et al., Ed.), E. & S. Livingstone, Edinburgh, pp. 199–206 (1970), herein incorporated by reference).

In a "simultaneous" assay, a single incubations step is employed in which the bound BV-55 and the labeled BV-55 are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In a "reverse" assay, a solution of labeled BV-55 is incubated with the sample, and the reaction is then placed in contact with a solid support to which unlabeled BV-55 has been previously bound. After a second incubation, the solid phase is washed in a conventional fashion to free it from the residue of the sample being tested and the solution of unreacted labeled BV-55. The determination of antibody titer is determined as in the "simultaneous" and "forward" assays.

In its most preferred embodiment, the ELISA of the present invention employs a monoclonal antibody. Most preferably, such antibodies are generated, as described above, by immunizing a heterologous mammal (such as a mouse, rat, rabbit, etc.) with BV-55, and then harvesting the splenic leukocytes of the animal, and fusing them with a suitable myeloma cell, in the manner described above.

Although the immunoassay has been described with respect to a particular preferred solid support, any of a variety of alternative solid supports may be employed. Suitable solid supports may be composed, for example, of materials such as glass, paper, polystyrene, polypropylene, polyethylene, dextran, nylon, amylases, natural and modified celluloses, polyacrylamides, agaroses, or magnetite. The nature of the support can be either soluble to some extent or insoluble for the purposes of the present invention. The support material may have virtually any possible structural configuration so long as the BV-55 molecules are capable of binding to antibody. Thus, the support configuration may be spherical, as in a bead, or cylindrical, as in the inside surface of a test tube, or the external surface of a rod. Alternatively, the surface may be flat such as sheet, test strip, etc. Those skilled in the art will note many other suitable carriers for binding monoclonal antibody, or will be able to ascertain the same by use of routine experimentation.

Having now generally described the invention, the same will be more readily understood through reference to the following examples which are provided by way of illustration, and are not intended to be limiting of the present invention, unless specified.

EXAMPLE 1

Cloning of BV-55

The 1700 bp EcoRi fragment (obtainable by Eco RI digestion of the above-identified deposited λgt11-P3 vector, ATCC 40378) coding for the rabbit 55 kD protein was subcloned into the Eco RI site present in the multiple cloning cassette in the BamHI site of the polyhedrin gene of the plasmid transfer vector PVL 1393. This site is downstream of the polyhedrin promoter. With the PVL 1393 transfer vector, translation is initiated from the ATG of the cDNA and not that of the polyhedrin gene, thus resulting in a non-fusion recombinant protein.

The plasmid DNA was purified on a cesium chloride gradient. The plasmid containing the cDNA in the correct reading frame with respect to initiation of the polyhedrin gene was selected and purified for transfection. The plasmid was designated "PVL-55." PVL-55 DNA (3 μg) was transfected into Sf9 insect cells along with 1 μg of wild type linear *Autographa californica* nuclear polyhedrosis virus ("AcMNPV") viral DNA (obtained from Invitrogen, San Diego, Calif.) by the cationic liposome transfection method, which increases the percentage of recombinant plaques obtained. 1.5×10$^6$ cells were seeded in 60 mm$^2$ petri dishes and the transfection mix was added dropwise to the culture cells and allowed to incubate for 48 hours.

The Sf9 cells were propagated in TNM-FH medium (Grace's insect media containing 3.33 g/l lactalbumin hydrolysate and 3.33 g/l yeastolate (JRH Biosciences, Lenexa, Kansas)) containing 10% fetal bovine serum at 28° C. and procedures for cell culture, viral infection and isolation of recombinant virus were carried out as described by (Summers M.D. et al., In: *A Manual of Methods for Baculovirus Vectors and Insect Cell Culture Procedures*, Texas Agricultural Experiment Station Bulletin No. 1555 (1987)).

Approximately 30% of the plaques were recombinant by plaque assay and were further purified by plaque assay as described by Summers M.D. et al. (In: *A Manual of Methods for Baculovirus Vectors and Insect Cell Culture Procedures*, Texas Agricultural Experiment Station Bulletin No. 1555 (1987)). The presence of the 1.7 kb cDNA fragment in the recombinant virus was confirmed by dot hybridization using $^{32}$P labeled cDNA.

The resulting recombinant baculovirus (designated "BV-55") was capable of expressing the BV-55 glycoprotein. The "BV-55" recombinant baculovirus was deposited with the American Type Culture Collection, 12301 Parklawn Drive 20852 Rockville, Md. U.S., on Aug. 2, 1994, as deposit Deposit. Accession No. VR2467

EXAMPLE 2

Expression of BV-55

The recombinant protein, BV-55 was expressed in insect cells according to the procedure of Jarvis, D. L. et al. (*Molec. Cell. Biol.* 9:214–223 (1989) herein incorporated by reference). Briefly, Sf9 cells were seeded at a density of 10$^6$ cells in a six well plastic culture dish and allowed to attach for 1 hour at 28° C. The medium was removed and the cells were infected with the recombinant virus obtained in Example 1 at a multiplicity of infection (MOI) of 10 for 1 hr. The inoculum was removed and replaced with 1 ml of TNM-FH+10% FBS medium, the infected cells cultured for 48 hr at 28° C. and the cells processed into three cellular fractions as follows:

Extracellular fraction consisted of medium recovered from cells after centrifugation at 1000× g for 5 min. and supplemented with NP-40 to 1% final concentration;

Intracellular fraction was prepared by the resuspending the cell pellet in 50 mM Tris pH 8.0 containing 100 mM NaCl and 1% NP-40, incubating on ice for 20 min. and microcentrifuging the extract for 15 min. to obtain the supernatant constituting the intracellular fraction;

Insoluble fraction was prepared by boiling the pellet from the intracellular fraction in SDS sample buffer (50 mM CHES pH 9.5, 2% SDS, 10% glycerol).

All three fractions were subjected to one-dimensional ("1-D") 10% sodium dodecyl sulfate polyacrylamide gel electrophoresis ("PAGE") and immunoblot analysis by probing with guinea pig antibodies made against two-dimensional ("2-D") PAGE purified rabbit 55 kD ZP protein. 1-D electrophoretic analysis was conducted as described by Timmons, T. M. et al. (In: *Methods in Enzymology*, Academic Press, New York pp. 680–688 (1990)). Two dimensional electrophoretic analysis was conducted as described by Dunbar, B. S. (In: *Two-Dimensional Gel Electrophoresis and Immunological Techniques*, Plenum Press, New York (1987)). Native rabbit ZP protein was used as a control. The recombinant protein is not expressed in sufficient quantities to be detected by Coomassie blue staining although it is detectable in the intracellular and insoluble protein fractions by immunoblot analysis.

The proteins were therefore subjected to immunoblot analysis. Antibodies were generated and characterized as described by Schwoebel, E. D. et al. (*Biol. Reprod.* 47:857–865 (1992)). Antibodies were diluted 1:100 in TBS (10 mM Tris pH 7.4, 0.15M NaCl) containing 5% nonfat dry milk. The levels of antibodies produced against the native rabbit ZP proteins in sheep and guinea pigs was determined using the ELISA described by Drell, D. et al. (*Biol. Reprod.* 30:435–444 (1984)). Guinea pig antiserum to native rabbit ZP proteins and to 2D-PAGE purified 55 kD protein and rabbit antisera to native pig ZP proteins were used as positive controls for these assays. Antibodies to the native rabbit protein were obtained from rabbit ovaries (PelFreez Biological, Rogers, Ark.) in the manner described by and ZP was isolated as described by Wood, D. M. et al. (*Biol. Reprod.* 25:439–450 (1981)). The ZP glycoproteins were solubilized by heating for one hour at 68° C. and partially deglycosylated using EβGD (obtained from Boehringer Mannheim, Indianapolis, Ind., U.S.) as described by (Schwoebel, E. D. et al., *Biol. Reprod.* 47:857–865 (1992)).

The results of such analyses demonstrated that the 55 kD ZP antigen was expressed only within cells that had been infected with the recombinant virus of Example 1, and that greater than 90% of the cells were expressing the recombinant protein. Analysis of the culture media, intracellular fraction and the insoluble fraction from the infected cells for the expression of 55 kD recombinant protein (BV-55) further demonstrated that the 55 kD protein was expressed in the intracellular and insoluble fraction but not in the media.

Since BV-55 is expressed as an intracellular protein, infected cells were lysed by french press to release the protein for characterization. Sf9 cells at a density of 10$^6$ cells/ml were infected with the recombinant virus obtained in Example 1 and cultured for 48 h in suspension culture (Summers M. D. et al., In: *A Manual of Methods for Baculovirus Vectors and Insect Cell Culture Procedures*, Texas Agricultural Experiment Station Bulletin No. 1555 (1987)). Cells were harvested from culture by centrifugation at 1000× g for 15 min. and subjected to french press lysis as described by Schwoebel, E. et al. (*J. Biol Chem* 266:7214–7219 (1991)). The lysate was centrifuged at 35,000× g for 30 min. and the supernatant subjected to 1-D and 2-D PAGE and immunoblot analysis, along with heat solubilized and endo-β-galactosidase ("EβGD") treated rabbit ZP control proteins.

Samples were separated by high resolution 2-D PAGE and transferred to PVDF (Immobilon-P, Millipore, Bedford, Mass.) for immunoblot analysis as described by Dunbar, B. S. (In: *Two-Dimensional Gel Electrophoresis and Immunological Techniques*, Plenum Press, New York (1987)). Heat solubilized and EβGD treated rabbit ZP proteins and baculovirus-expressed recombinant 55 kD protein were separated on a 10% 1-D PAGE and either visualized by comassie blue or silver staining or electrophoretically transferred to PVDF membrane for immunoblot analysis as described by Timmons, T. M. et al. (In: *Methods in Enzymology*, Academic Press, New York pp. 680–688 (1990)) using antibodies from rabbits immunized with total heat solubilized pig ZP or guinea pig antibodies to 2-D PAGE purified rabbit 55 kD ZP protein or antibodies to BV-55 protein generated in rabbits and guinea pigs.

The BV-55 protein was found to migrate as two bands (70 kD and 80 kD) by both 1-D and 2-D immunoblot analysis. One dimensional PAGE immunoblots of the supernatant of infected cell lysates containing the BV-55 protein revealed that BV-55 had a molecular weight similar to that of the enzyme deglycosylated rabbit 55 kD protein although the apparent molecular weight was less than that of the native glycosylated rabbit ZP protein. The BV-55 protein was found to have an apparent pI that was more basic (relative pI of 6.0–9.0) than the native ZP protein (relative pI of 3.8–6.5).

EXAMPLE 3

Immunocytochemical Localization

Sf9 cells and the cells infected with the recombinant virus of Example 1 were subjected to immunohistochemistry using guinea pig anti-55 kD ZP protein antibodies in order to demonstrate the expression of 55 kD ZP protein.

Thus, Sf9 cells were infected with the recombinant virus of Example 1 and cultured for 48 hours. The cells were harvested by centrifugation at 1000× g for 10 min. The cell pellet from infected cells and Sf9 cells alone were fixed in 4% buffered paraformaldehyde solution and embedded in 2% agarose. The pellets were dehydrated and embedded in paraffin and sectioned. The sections were subjected to immunohistochemistry as described by Skinner, S. M. et al. (*J. Histochem. Cytochem.* 40:1031–1036 (1992)). Sections were blocked with normal goat antiserum (1:200) in 0.1% BSA and treated with guinea pig anti-rabbit 55 kD ZP antibodies (1:100).

Sections were then treated with biotinylated goat anti-guinea pig IgG (1:200) and the signal was developed using the avidin-biotin system of Vector Laboratories (Burlingame, Calif.) and 3,3'-diaminobenzidine as chromophore. Antibodies to total heat solubilized pig ZP were generated in rabbits and characterized as described by Wood, D. M. et al. (*Biol. Reprod.* 25:439–450 (1981)).

These analyses collectively demonstrated that BV-55 protein was expressed in the infected cells although it was not secreted at significant levels. These studies further demonstrated that BV-55 protein was expressed as two molecular weight forms (70K and 80K) which were both recognized by rabbit anti-pig ZP and guinea pig anti-rabbit 55 kD antisera (produced as described by Schwoebel, E. D. et al., *Biol. Reprod.* 47:857–865 (1992)) as compared to proteins of the uninfected control Sf9 cell lysate.

EXAMPLE 4

Optimization of Expression of BV-55

In order to maximize the expression of the recombinant protein, insect cells were infected with the recombinant virus of Example 1 at a MOI of 1, 5, and 10, and the level of BV-55 in the intracellular fraction was determined as described above. There was no apparent difference in the level of expression as detected by immunoblot analysis. The cells were therefore routinely infected at MOI of 5-10.

Synthesis of BV-55 was studied by incubating infected cells at 24 h, 48 h, and 72 h post infection in the presence of $^{35}$S-translabel (ICN, Irvine, Calif.). The infected cells were seeded at a density of $10^6$ cells per well in a six well culture dish. The cells were first incubated in methionine-free Grace's insect media (Gibco, Grand Island, N.Y.) for 30 min. and then incubated in 1 ml of the same media containing 30 µCi of $^{35}$S translabel for 4 h. A similar procedure was followed for control cells that were not infected with the recombinant virus of Example 1.

The $^{35}$S labeled intracellular fraction obtained as described above was incubated with 20 µl of normal rabbit serum for one hour to reduce non-specific binding followed by incubation with 25 µl of a 10% solution of protein A sepharose (Pharmacia, Piscataway, N.J.) for one hour. The incubation mixture was microcentrifuged for 5 min., washed with buffer (50 mM Tris pH 7.2, 150 mM NaCl, 0.5% NP-40) and the supernatant was incubated with 25 µl of rabbit anti-pig ZP antibodies overnight at 4° C. It was then incubated with 25 µl of 10% protein A sepharose solution for one hour at room temperature. The mixture was microcentrifuged, washed and the supernatant subjected to PAGE and stained with comassie blue. The gel was incubated in Enhance (ICN, Irvine, Calif.) for one hour, washed in water, vacuum dried and flurographed.

The immunoprecipitated labeled BV-55 protein was analyzed by PAGE and fluorography. BV-55 was found to be expressed in greater amounts at 24 h and 48 h while at 72 h the levels of protein were decreased. The infected cells were therefore cultured for 48 h throughout these studies.

EXAMPLE 5

Glycosylation of BV-55

In order to determine if the two molecular weight forms of BV-55 were the result of differential glycosylation, studies were carried out by culturing the infected cells in the presence of $^{35}$S translabel to evaluate protein synthesis in the presence or absence of tunicamycin, which inhibits N-linked glycosylation (Takatsuki, A. et al., *Agri. Biol. Chem.* 39:2089–2091 (1975)).

Thus, approximately $10^6$ Sf9 cells were seeded in a six well culture dish and infected with the recombinant virus of Example 1. At 48 h post infection, the media was removed and cells were cultured in methionine-free Grace's insect media for 30 min. The media was removed and the cells incubated in methionine free Grace's insect media containing 30 µCi of $^{35}$S translabel in the presence or absence of 2 µg of tunicamycin (Sigma, St. Louis, Mo.) for 4 h at room temperature. The cells were then plated at a density of $10^6$ cells/well in a six well culture dish and cultured in the presence of 1 μg/ml, 2 μg/ml, and 5 μg/ml of tunlcamycin for 48 h. After such incubation, the cells were harvested by centrifugation and the intracellular fraction was obtained as described above. The labeled expressed protein was immuno-precipitated using rabbit anti-pig ZP antibodies and subjected to PAGE and fluorography.

Analysis of the labeled expressed protein at 48 h post infection demonstrated the presence of the 70 kD form when cells were cultured for 4 h in the presence of tunlcamycin as compared to cells cultured in the absence of tunicamycin which have both 70 kD and the 80 kD forms. Similar results were obtained when infected cells were cultured for 48 h in the continued presence of tunicamycin and the intracellular protein fraction analyzed by PAGE and the immunoblot analysis. Only the 70 kD molecular weight form was present in the intracellular protein fraction of infected cells incubated with tunicamycin while, in the absence of this N-linked glycosylation inhibitor, both the 70 kD and the 80 kD forms were present. There was no substantial difference in the level of expression of BV-55 protein in infected cells cultured in the presence of different concentrations of tunicamycin.

In order to further characterize the N-linked glycosylation of BV-55, supernatant of cell lysate of infected and uninfected insect cells were separated by electrophoresis and subjected to lectin blot analysis using biotinylated lectins. Thus, the supernatants from infected and uninfected Sf9 cell lysates prepared as described above as well as heat solubilized rabbit ZP were separated on a 10% SDS polyacrylamide gel and the proteins were electrophoretically transferred to PVDF membrane. The blot was blocked in TBST buffer (10 mM Tris pH 7.4, 150 mM NaCl, 0.1% Tween 20) for at least one hour. The blot was then incubated with 10 μg/ml of biotinylated lectins (Vector Laboratories, Burlingame, Calif.) in TBST for one hour, washed three times with TBST and detected with avidin-biotin system (Vectastain kit, Vector Laboratories) using horseradish peroxidase and 3,3'diaminobenzidine as the chromophore.

Wheat germ agglutinin (WGA), which recognizes N-acetylglucosamine oligosaccharides was found to recognize carbohydrates associated with the BV-55 protein. An 80 kD protein was observed in the lysate of uninfected cells (i.e., cells that do not express the BV-55 protein) which comigrates with the 80 kD BV-55 protein. This protein from uninfected cells was also recognized by WGA. Similarly, Concanavalin A (Con A) which recognized mannose containing oligosaccharides bound to BV-55 protein as well as to other insect cell lysate proteins. RCA 120, SBA and PNA lectins did not appear to recognize carbohydrates on the BV-55 protein. Table 1 summarizes the lectin binding properties of BV-55 (using an unfractionated mixture of the 70 kD and 80 kD molecular species) as compared to the native rabbit ZP protein. The comparison of lectin binding properties of BV-55 protein with native rabbit ZP proteins revealed that BV-55 has core mannose and N-acetylglucosamine type oligosaccharide structures but lacks N-acetylgalactosamine type oligosaccharide structures. Further studies used a monoclonal antibody (PS1) that is specific to a carbohydrate epitope (lactosaminoglycan type structure) (Timmons, T. M. et al., In: *Gamete Interaction: Prospects for Immunocontraception* (Alexander N et al., eds) John Wiley & Son, N.Y.; pp. 277–292 (1990)) associated with all of the major rabbit ZP proteins to test recognition of the BV-55 protein (Table 1). These studies demonstrated that the PS1 epitope was not associated with the BV-55 protein. In Table 1, a "+" denotes the presence of the recognized carbohydrate; a "−" denotes the substantial absence of the recognized carbohydrate.

TABLE 1

| Lectin/MAb | Carbohydrate Recognition | BV-55 | Native Rabbit ZP |
|---|---|---|---|
| Concanavalin A | α-Mannose α-Glucose | + | + |
| Soybean Agglutinin (SBA) | α or β linked N-Acetyl Galactosamine | − | − |
| Wheat Germ Agglutinin (WGA) | N-Acetyl Glucosamine | + | + |
| Peanut Agglutinin (PNA) | Galactosyl N-Acetyl Galactosamine | − | − |
| Ricinus Communis Agglutin I (RCA 120) | α-Galactose N-Acetyl Galactosamine | − | + |
| MAb PS1 | Lactosaminoglycan Structure | − | + |

EXAMPLE 6

Protein Purification For Immunogenicity Studies

Since the lectin, WGA, binds to carbohydrates associated with the BV-55 protein, it was used to further purify the recombinant protein through affinity chromatography.

Approximately $2 \times 10^8$ infected Sf9 cells were harvested by centrifugation at 1000×g for 15 min. and the cell pellet resuspended in 5 ml of WGA buffer (20 mM Tris pH 7.4, 150 mM NaCl, 1 mM $MgCl_2$ and 1 mM $CaCl_2$) were lysed by french press (American Instrument Co., Silver Spring, Md.). The supernatant was centrifuged at 35,000 rpm for 30 min. at 4° C., and then applied to a wheat germ agglutinin (WGA) agarose column and allowed to equllibrate by end over end rotation overnight at 4° C. The unbound eluate was collected and the column washed with three column volumes of WGA buffer. The bound protein was eluted using 5 ml of 0.5M N-Acetylglucosamine in WGA buffer. The yield of the resultant protein was approximately 0.5 mg.

In order to determine whether glycosylation enhanced the immunogenicity of the recombinant 55 kD protein, BV-55 protein was used as an immunogen. Female guinea pigs were immunized by intradermal injections of either 150 μg of BV-55 protein eluted from WGA column (three animals) or with 500 μg of the supernatant from uninfected Sf9 cell lysate (three animals). The animals were given a booster dose of the same amount subcutaneously four weeks after the primary immunization. Two weeks later 3 ml of blood was collected by cardiac puncture under anesthesia according to approved animal protocols. After the initial detection of antibodies to the 55 kD rabbit ZP protein by immunoblot analysis, guinea pigs were immunized every four weeks for 16 weeks and the animals were bled every two weeks.

For rabbit studies, sexually mature female rabbits (three) were immunized with either 0.5 mg of BV-55 protein (french press supernatant) or with 0.5 mg of supernatant of uninfected Sf9 cell lysate (two rabbits). Primary immunization was given intradermally at multiple sites with CFA under anesthesia, while the booster dose (0.5 mg) was given subcutaneously four weeks after the initial immunization. Animals were bled two weeks after the boost by the ear vein and 5 ml of blood was collected. The serum was used in immunoblot analysis to determine the presence of antibodies to the 55 kD rabbit ZP protein.

The BV-55 immunogen was found to have elicited a significant immune response in both the rabbits and guinea pigs as evaluated by detectable antibodies that recognize the native as well as the enzyme deglycosylated EβGD-treated rabbit 55 kD ZP protein on 1-D PAGE immunoblot. Antibodies to the native rabbit protein were obtained as described above. The electrophoretic analysis was performed as described above.

Control antisera from rabbits or guinea pigs immunized with the supernatant of uninfected Sf9 cell lysate did not recognize rabbit ZP proteins. Two of the rabbits developed detectable antibodies, while all three guinea pigs developed high titer antibodies to the 55 kD protein. Using 2-D PAGE immunoblot analysis, the rabbit anti-BV-55 and guinea pig anti-BV-55 antibodies were also shown to be specific for the 55 kD native rabbit ZP protein.

The anti BV-55 guinea pig sera were further analyzed by ELISA to determine if the antibody levels to native ZP were sustained over time. As seen from the data summarized in Table 2, all three guinea pigs developed significant antibody titers that were maintained with the immunization schedule described above. In Table 2, titers are determined as final dilution giving positive reading over Sf9 control serum; animals received booster doses of BV-55 at 19, 23, and 27 weeks.

TABLE 2

| Weeks Post-Innoculation | Antibody Titer of Guinea Pig | | |
|---|---|---|---|
| | GP #4 | GP #5 | GP #6 |
| 4 | 0 | 0 | 0 |
| 6 | 16,000 | 16,000 | 16,000 |
| 8 | 16,000 | 16,000 | 16,000 |
| 19 | 128,000 | 64,000 | 32,000 |
| 21 | 64,000 | 32,000 | 32,000 |
| 23 | 128,000 | 64,000 | 32,000 |
| 25 | 128,000 | 32,000 | 32,000 |
| 27 | 128,000 | 32,000 | 32,000 |
| 29 | 128,000 | 32,000 | 32,000 |

When guinea pig antibody titers elicited in response to BV-55 were compared with those elicited by native and bacterially-expressed 55 kD protein, BV-55 protein was found to be more immunogenic than non-glycosylated pEX expressed recombinant 55 kD protein (Table 3). In addition, these studies show that the relative guinea pig antibody titers are greater than those of cynomolgus monkey antisera generated from immunization with rec55 protein expressed in pEX bacteria and conjugated to protein A (Schwoebel, E.D. et al., *Biol. Reprod.* 47:857–865 (1992)). In Table 3, "(a)" denotes data from Skinner, S.M. et al. (*J. Reprod. Immunol.* 12:81–92 (1987)); "(b)" denotes data from Lee. V.H. et al. (Dev. Biol. 155:371–382 (1993)); "(c)" denotes data from Schwoebel, E.D. et al. (*Biol. Reprod.* 47:857–865 (1992)).

TABLE 3

| Immunogen | Animal Immunized | Antibody Production ELISA/immunoblot |
|---|---|---|
| HSRZ | Rabbit (a) | – – |
| Rabbit 55 kD | Guinea Pig (b) | + + |
| pEX-rec55 | Rabbit (c) | – – |
| pEX-rec55 | Guinea Pig | – – |
| pEX-rec55 | Cynomolgus Monkey (c) | – – |
| pEX-rec55 + Protein A | Cynomolgus Monkey (c) | + + |
| BV-55 | Rabbit | + + |
| BV-55 | Guinea Pig | + + |

A similar experiment was performed using cynomolgus monkeys. Animals were immunized with either adjuvant alone ("Control" group) or with adjuvant plus 0.3 mg/animal of BV-55 ("BV-55" group) or with adjuvant plus the non-glycosylated pEX expressed recombinant 55 kD protein (the "rec55-pEX" group). Adjuvant was 10% sqalene, 5% pluoronic acid L121 in phosphate buffered saline (pH 7.2) containing 0.4% Tween 80. The antibody titers were determined using ELISA assay on native rabbit ZP. The results of this experiment are shown in FIG. 1. As shown in FIG. 1, immunization with BV-55 resulted in high anti-ZP antibody titers. All of 8 animals tested exhibited such a response.

EXAMPLE 7

Characteristics of BV-55

The BV-55 protein has been found to be expressed but not secreted by Sf9 cells even though the encoding cDNA has a well defined signal peptide and insect cells are known to have the machinery for cleavage and protein secretion. It thus appears that the hydrophobic nature of the BV-55 glycosylated protein causes the protein to become associated with cell membranes.

As indicated above, the BV-55 protein is expressed as two distinct proteins having relative molecular weights of 70 kD and 80 kD. This heterogeneity appears to be due to differential glycosylation as demonstrated by the glycosylation inhibition obtained with tunicamycin. These molecular weights, however, are still lower than that of the native 55 kD glycosylated ZP protein which has an apparent molecular weight of 75–90 Kd. Therefore, the glycosylation pattern of the BV-55 protein appears to be distinct from that of the native protein. Similarly, it has been demonstrated that mouse ZP3, expressed in eukaryotic cell lines (mouse L-929 cells and green monkey CV-1 cells) results in a recombinant protein with an apparent molecular weight which is lower than that of the native protein (Beebe, S.J. et al., *Dev. Biol.* 151:48–54 (1992)). Furthermore, differential glycosylation has also been observed when mouse and hamster ZP3 were expressed in embryonal carcinoma cells (Kinloch, R.A. et al., *J. Cell. Biol.* 115:655–664 (1991)). The recombinant mouse ZP3 exhibited mouse sperm binding and acrosome-inducing activities, whereas the hamster ZP3 did not (Kinloch, R.A. et al., *J. Cell. Biol.* 115:655–664 (1991)). However, transgenic mouse oocytes containing the hamster ZP3 gene synthesized and secreted glycosylated biologically active hamster ZP3 (Kinloch, R.A. et al., *Devel.* 115:937–946 (1992)). It therefore appears that different eukaryotic cells may glycosylate ZP proteins very differently and that these differences may affect some functions of these proteins.

Although the BV-55 protein is glycosylated differently than the native rabbit ZP protein, a similar N-linked glycosylation pattern was observed by lectin blot analysis (Table 1). Both have mannose and N-acetylglucosamine type oligosaccharide structures, but lack N-acetylgalactosamine type structure. In addition, inhibition of N-linked glycosylation using tunicamycin, results in the expression of only the 70 kD form. Since this protein has an apparent molecular weight of 57 kD which is greater than that of the native core protein, it appears that some O-linked oligosacharide residues may also be present. Finally, it is apparent that the glycosylation of BV-55 protein is distinct from the native ZP protein since a monoclonal antibody specific to a carbohydrate epitope (lactosaminoglycan) that recognizes all major rabbit ZP proteins does not recognize the BV-55 protein.

In order to determine if the differences in glycosylation of the recombinant ZP protein altered its immunogenicity, female rabbits and guinea pigs were immunized with the BV-55 protein. Previous studies have demonstrated that alloimmunization of female rabbits with rabbit ZP proteins does not result in detectable serum antibody titers (Skinner, S.M. et al., *J. Reprod. Immunol.* 12:81–92 (1987)). However, as shown above, immunization of rabbits with the recombinant BV-55 protein induced significant antibody titers. This suggests that the glycosylation of the recombinant BV-55 ZP protein is sufficiently different from the native rabbit ZP glycoprotein to elicit antibody production. A previous observation also showed that female rabbits immunized with rec55 protein (pEX bacterially expressed nonglycosylated 55 kD recombinant protein) (Schwoebel, E.D. et al., *Biol. Reprod.* 47:857–865 (1992)) did not produce detectable serum antibodies. Although the titer of the antibodies produced in rabbits against the BV-55 protein is relatively low, these antibodies recognized determinants associated with the native 55 kD ZP antigen when analyzed by both 1-D and 2-D PAGE immunoblots. However, guinea pigs immunized with BV-55 protein developed relatively high antibody titers as compared to antibody levels in sera of animals immunized with the native 55 kD protein. These antisera recognize the enzyme deglycosylated as well as native glycosylated 55 kD ZP protein. In contrast, guinea pigs immunized with rec55 protein expressed in bacteria did not develop antibodies to native 55 kD protein. BV-55 elicited anti-ZP antibodies in 8 of 8 inoculated baboons, thus indicating that the BV-55 immunogen is effective in primates.

Thus, a molecular approach was used to evaluate the immunogenicity of glycosylated and non-glycosylated recombinant rabbit 55 kD ZP protein. The 55 kD cDNA was expressed in Sf9 insect cells using a recombinant baculovirus-rec55 construct to obtain the non-fusion, glycosylated BV-55 recombinant ZP protein. electrophoretic and immunoblot analysis showed that the BV-55 protein was expressed as two molecular weight forms (of approximately 70 k and 80 k). In order to evaluate the extent of glycosylation of this protein in this eukaryotic expression system, lectin blot and immunoblot analyses were performed. These studies showed that the BV-55 protein had core mannose and N-acetylglycosamine type oligosaccharide structures that were similar to those of the native protein, but that BV-55 lacked N-acetylgalactosamine type oligosaccharide structures. In addition, BV-55 was not recognized by a monoclonal antibody that recognized a lactosaminoglycan-associated carbohydrate epitope in native ZP glycoproteins. Immunogenicity studies showed that antibodies against the BV-55 protein were developed by female rabbits and guinea pigs while recombinant protein expressed in bacteria did not induce antibody production. These anti BV-55 antibodies recognized epitopes associated with native as well as enzyme deglycosylated rabbit 55 kD ZP protein. Because BV-55 protein elicits antibodies in female rabbits in contrast to the native rabbit ZP proteins, it is apparent that the foreign glycosylation of BV-55 protein is responsible for the enhanced immunogenicity.

Collectively, these studies demonstrate that glycosylation of the recombinant rabbit ZP protein using the baculovirus expression system enhances immunogenicity. Furthermore, this glycosylation appears to be sufficiently distinct from the native glycosylation in that it makes rabbit ZP protein immunogenic in female rabbits, guinea pigs, and baboons.

EXAMPLE 8

Ability of BV-55 to Bind to Sperm Receptors

ZP proteins which act as receptors for homologous sperm have been described for a number of species, and have been shown to be important candidates in the development of a contraceptive vaccine. However, obtaining such proteins on a quantity and a purity sufficient to allow detailed characterization of biological activity has frequently been complicated by the extreme heterogeneity of the native proteins due to extensive post-translational modifications.

The above-described examples describe the use of a eukaryotic baculovirus expression system to express a cDNA molecule that encodes the 55 kD rabbit ZP protein. The resultant recombinant protein, BV-55 was expressed as a soluble, partially glycosylated protein. BV-55 was purified by lectin affinity chromatography.

The purified protein was used to immunize guinea pigs, or was biotinylated and tested for its ability to bind to rabbit sperm directly. Both the guinea pig antiserum ("GP-α-BV-55") and Fab fragments purified from this serum ("Fab-α-BV-55") were found to recognize native (R55) protein and recombinant (r55) by one-and two-dimensional immunoblotting and ELISA techniques.

Biotinylated BV-55 was found to be able to bind to capacitated rabbit sperm in vitro binding experiments. The biotinylated protein localized to the anterior portion of the sperm head in the acrosomal region. Occasional labeling of equatorial segments was also observed, and these sperm were presumed to be acrosome reacted.

EXAMPLE 9

Ability of anti-BV-55 Antibodies to Prevent Fertilization

The ability of BV-55 to elicit antibody that could block fertilization was investigated using the above-described GP-α-BV-55 antibodies and Fab-α-BV-55 antibody fragments. Antisera from guinea pigs immunized with Sf9 insect extract was also prepared "GP-α-Sf9"), and used as a control. Antisera from sheep immunized with heat solubilized rabbit ZP was also used a control ("S-α-hsRZ").

Eggs were incubated overnight in the cold in solutions of antibody (diluted 1:50, 1:5 or 1:1). Sperm ($10^5$) were added, and the binding of sperm to egg was allowed to proceed for one hour. The eggs were then washed, and the number of sperm bound per egg was determined. The results of this experiment are shown in FIG. 2.

Figure 2:
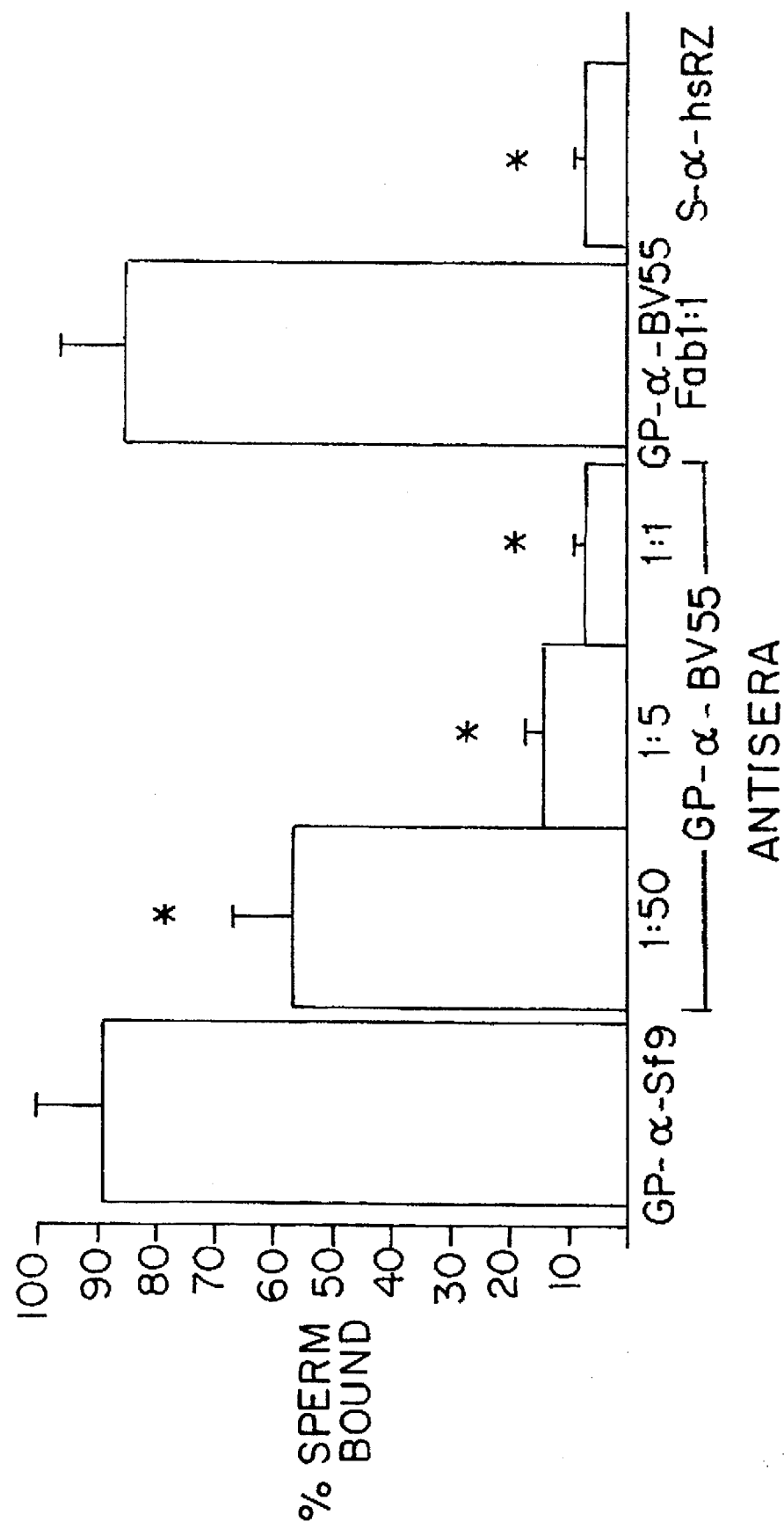

Significantly, as shown in FIG. 2, GP-α-BV-55 was found to be able to inhibit rabbit sperm from binding to rabbit eggs in vitro, in a dose dependent manner. This Fab-α-BV-55, however, failed to block sperm binding, suggesting that the inhibitory effect of the serum was due to steric hindrance, rather than a blocking of a specific sperm ligand site. Egg cells that had been incubated in the presence of GP-α-BV-55 exhibited dark (precipitin) rings on the periphery of the ZP, indicating the binding of large quantities of antibody. Such rings were not observed to surround eggs that had been incubated with control antibodies. These findings indicate that BV-55 impairs the capacity of sperm to bind to egg cells and indicate that BV-55 may be used as a contraceptive immunogen. As expected, the S-α-hsRZ control antibody was able to prevent sperm-egg binding. As shown in FIG. 2, the GP-α-BV-55 antibody reduced the percentage of sperm bound to egg by 90%.

Therefore, the expression of specific ZP protein(s) as well as specific sperm antigens in insect cells using recombinant baculovirus provides excellent immunogens for immunocontraception in other animals and particularly in humans.

EXAMPLE 10

Histological Evaluation of Ovarian Tissue

As discussed above, antibodies elicited in response to ZP immunogens have been found to impair the development of ovarian follicular cells, or to decrease the number of follicular cells produced. In order to ascertain whether the antibodies elicited in response to BV-55 immunizations would interfere with ovarian development, histologic evaluations of BV-55-immunized guinea pig and cynomologus monkeys was conducted.

For such studies, the ovaries of guinea pigs immunized with BV-55 were fixed with Bouin's fixative or paraformaldehyde fixative and were imbedded in paraffin as described above and evaluated for indication that follicle development had been impaired or that the number of follicles had been affected. The analyses revealed the presence of cells at all stages of follicular development. No evidence of pathology were observed.

Cynomolgus monkeys were also immunized with BV-55, and developed anti-BV-55 antibodies. The animals exhibited normal ovulatory cycles from the time of immunization to the present (a period of approximately six months).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A contraceptive vaccine comprising:

(A) glycosylated 55 kD rabbit zona pellucida protein immunogen, wherein said protein is BV-55 and is obtainable by expression of recombinant baculovirus BV-55 in insect cells selected from the group consisting of Sf9 cells, SF21 cells and MG1 cells, wherein said baculovirus BV-55 has the ATCC Accession No. VR-2467, wherein said immunogen lacks a lactosaminoglycan type structure, wherein said immunogen is present in an amount effective to produce antibodies in a mammalian female recipient, and wherein said antibodies inhibit the binding of sperm to egg cells by binding to the zona pellucida of said female's oocytes, but do not interfere with development of said female's follicular cells or with the number of follicular cells produced; and (B) a pharmaceutically acceptable carrier or diluent.

2. A method of contraception which comprises administering to a mammalian female a contraceptive vaccine comprising glycosylated 55 kD rabbit zona pellucida protein immunogen and a pharmaceutically acceptable carrier or diluent, wherein said protein is BV-55 and is obtainable by expression of recombinant baculovirus BV-55 in insect cells selected from the group consisting of Sf9 cells, SF21 cells and MG1 cells, wherein said baculovirus BV-55 has the ATCC Accession No. VR-2467, wherein said immunogen lacks a lactosaminoglycan type structure, wherein said immunogen is present in an amount effective to produce antibodies in a mammalian female recipient, and wherein said antibodies inhibit the binding of sperm to egg cells by binding to the zona pellucida of said female's oocytes, but do not interfere with development of said female's follicular cells or with the number of follicular cells produced.

* * * * *